(12) United States Patent
Matsumoto et al.

(10) Patent No.: US 7,901,631 B2
(45) Date of Patent: *Mar. 8, 2011

(54) UNIT FOR MEASURING ABSORBANCE

(75) Inventors: Shigeki Matsumoto, Himeji (JP);
Shigenori Nozawa, Himeji (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 1014 days.

This patent is subject to a terminal disclaimer.

(21) Appl. No.: 11/225,044

(22) Filed: Sep. 14, 2005

(65) Prior Publication Data
US 2006/0061759 A1  Mar. 23, 2006

(30) Foreign Application Priority Data
Sep. 22, 2004  (JP) .................................. 2004-274788

(51) Int. Cl.
*G01N 21/00* (2006.01)
*G01N 21/01* (2006.01)
(52) U.S. Cl. ..................... 422/82.09; 422/82.11; 356/244
(58) Field of Classification Search ............... 422/82.11, 422/110
See application file for complete search history.

(56) References Cited

U.S. PATENT DOCUMENTS

| | | | |
|---|---|---|---|
| 5,013,155 A | 5/1991 | Rybak | |
| 7,443,502 B2 * | 10/2008 | Nozawa et al. | 356/244 |
| 7,636,162 B2 * | 12/2009 | Ogawa et al. | 356/399 |
| 2002/0015667 A1 | 2/2002 | Chow | |
| 2002/0064800 A1 | 5/2002 | Sando et al. | |
| 2003/0091477 A1 * | 5/2003 | Paul et al. | 422/104 |
| 2006/0061760 A1 * | 3/2006 | Matsumoto et al. | 356/246 |

FOREIGN PATENT DOCUMENTS

| | | | |
|---|---|---|---|
| EP | 1338890 A1 * | 8/2003 | |
| JP | 2004-077305 | 3/2004 | |
| JP | 2004077305 A * | 3/2004 | |
| JP | 2004-109099 | 4/2004 | |
| WO | WO 03/004162 A1 | 1/2003 | |
| WO | WO 03078979 A1 * | 9/2003 | |

* cited by examiner

*Primary Examiner* — Sam P Siefke
*Assistant Examiner* — Bryan T Kilpatrick
(74) *Attorney, Agent, or Firm* — Roberts Mlotkowski Safran & Cole, P.C.; David S. Safran

(57) ABSTRACT

A unit for measurement of absorbance using a microchip has a microchip with a continuous cavity, a sample chamber, a reagent chamber, a reagent mixing chamber and a chamber for measuring absorbance, which is arranged in a straight line in the area of the continuous cavity. The microchip is located in a chip holder which has a capillary part which is arranged such that the light used to measure absorbance is delivered through the capillary part to the chamber for measuring absorbance, the capillary part having a smaller opening diameter than the diameter of the cross section which is perpendicular to the optical axis of the chamber for measuring absorbance.

12 Claims, 6 Drawing Sheets

$$\frac{D_1}{L_1} \leq \frac{D_2-D_1}{2L_2} \quad \text{(however, } D_1 < D_2\text{)}$$

UNIT FOR MEASURING ABSORBANCE

BACKGROUND OF THE INVENTION

1. Field of the Invention

The invention relates to a unit for measuring absorbance using a microchip to execute solution analysis by an absorption spectrum process.

2. Description of Related Art

Recently an analysis method using a microchip called μ-TAS or Lab-on-a-chip has been considered in which, using precision processing technology of semiconductors and a technology for producing micromachines, chemical analyses and the like are performed in a more precise manner as compared to conventional devices. In the case of using μ-TAS for medical fields there are the following advantages:

(1) By reducing the amount of sample, such as, for example, blood, the burden on the patient can be reduced.

(2) By reducing the amount of reagent, the study costs can be reduced.

(3) Since the device is small, the study can be easily carried out.

By analysis using the absorption spectrum process with a microchip, the concentration of a desired enzyme which is contained in the blood plasma can be measured by the series of operations described below.

(1) Blood which was taken using a painless needle is delivered into the chip.

(2) The blood in the chip undergoes centrifugal treatment and is divided into plasma and hematocytes.

(3) The plasma and reagent are uniformly mixed with one another using a mixer and a mixture is produced therefrom.

(4) The mixture is delivered by means of a suction pump into a chamber for measuring absorbance.

(5) The mixture which was delivered into the chamber for measuring absorbance is irradiated with light from a light source and the attenuation of the light at a certain wavelength is measured. This effort is the measurement of absorbance.

The method of analyzing the concentration of an enzyme which is contained in the blood, such as, for example, GTP (glutamyl trans-peptidase), γ-GTP or the like, and which is needed, for example, to diagnose liver function, is disclosed in Japanese patent disclosure document JP-2004-109099 A.

This publication shows a process in which light which is emitted from a light source, such as a light emitting diode or the like and which is incident from the top of the chip, which is totally reflected in an extremely small channel in the chip which is filled with an analysis sample, such as, for example plasma, and which emerges from the top of the chip, is measured with a detector such as a silicon photodiode or the like.

The light emitted by the light emitting diode is, however, scattered light. It is extremely difficult to subject the light incident in the chip to total reflection overall in an extremely small channel. Therefore, there is the disadvantage that the absorbance cannot be measured with high precision. The measurement of absorbance by the arrangement described in the aforementioned publication and the light source as well as of the detector on the top of the microchip causes the occurrence of measurement errors; this is not desirable.

On the other hand, as shown in FIG. 6, in Japanese patent disclosure document JP-2004-77305 A, a technique is described in which light from a light source can be incident from one side of a microchip, in which the light is absorbed by a sample, with which a channel 41 is filled, for determination in the microchip 40, and in which the fluorescence which emerges from the other side is determined. It can be imagined that, in a process for use of a channel for determination of a straight sample, the microchip measurement can be performed with high precision when absorbance is measured using blood as the sample.

In the case of using a microchip for measuring the concentration of a sample by an absorption spectrum process, the length of the optical path cannot be shortened because a certain amount of absorption is required. The surface of the light entry and exit areas of the part for measurement of absorbance is, for example, roughly 0.49 $mm^2$, i.e., very small. Therefore, a very narrow cell is needed. As a result, for exact measurement of absorbance, it is necessary for light with high parallelism to be incident. This is because, with high parallelism of the light, the light which passes through the side of the chamber and which emerges to the outside from the chamber for measuring absorbance is reduced and that measurement errors due to faulty light are reduced. Here, "faulty light" is defined as the light which passes through the chip part, but not through the chamber for measuring absorbance, and enters a light detector.

A laser can be imagined as an ideal light source. The wavelengths necessary for chemical analyses are however diverse. For laser light which is monochromatic light, for each required wavelength, a respective laser is needed. Costs are high. Therefore, lasers are not well suited to this function. It can also be imagined that there is no laser which emits the required wavelength. Therefore, as the light source, a light source is advantageous with an arrangement in which a discharge lamp, such as a xenon lamp or the like, which emits light in a continuous wavelength range is combined with a wavelength selection means, such as a wavelength selection filter or the like.

However, since the discharge lamp has a large arc spot and cannot emit parallel light with high efficiency, a measure is required against faulty light which passes through an area outside of the chamber for measuring absorbance and enters a light receiving apparatus. This is because the faulty light influences the measured value.

As a concept for incidence of light with little parallelism in the chamber of the microchip to measure absorbance, there is a process in which the inside of the chamber for measuring absorbance is coated with a fluororesin or with aluminum and in which the light is routed to the output using total reflection. Furthermore, there is also a process in which, on the end face of the chamber used to measure absorbance, a silica glass material is cemented and the substrate is made opaque to the measurement wavelength. As the means for delivery into the chamber for measuring absorbance, there is a process in which an optical fiber is inserted into the hole of the chip and total reflection is used within a cell.

In the process in which the inside of the chamber used to measure absorbance is coated, the light which is obliquely incident on the end face of the chamber used to measure absorbance is totally reflected from the inside and travels to the light receiving apparatus. Therefore, the optical path becomes longer than the length of the chamber used to measure absorbance, by which the transmission factor becomes less than in practice. As a result, the correct transmission factor cannot be measured. In the process in which the part, besides the end face, is made opaque, the light is totally reflected which has struck the side of the chamber used to measure absorbance with a flatter angle than the critical angle of total reflection, by which the optical path becomes longer than the length of the chamber for measuring absorbance. In this way, the transmission factor becomes less than in practice; this causes measurement errors. In a process in which the light is delivered using an optical fiber, the light emerging from the tips of the fibers propagates, by which reflection occurs within the chamber that is used to measure absorbance and there is the danger errors occur in the measurement values.

SUMMARY OF THE INVENTION

A primary object of the present invention is to devise a unit for measurement of absorbance using a microchip in which measurements can be achieved with few measurement errors even when using a discharge lamp as the measurement light source.

In accordance with a first aspect of the invention, in a unit for measurement of absorbance using a microchip which comprises the following:

a microchip which preferably comprises plate components which have been cemented together, between which there is a continuous cavity, and which has a part for delivering an analysis fluid (sample chamber), a reagent chamber, and a reagent and sample mixing chamber as well as a chamber for measuring absorbance, which is arranged in a straight line, preferably along the end face of the above described plate components; and a chip holder in which the microchip is installed, the above described object is achieved in that, in the chip holder, a capillary part is formed which brings the chamber for measuring absorbance and the optical axis into agreement, which has a smaller opening diameter than the diameter of the cross section which is perpendicular to the optical axis of the chamber for measuring absorbance and is used to deliver the light into the chamber for measuring absorbance.

The object is achieved in accordance with a further development of the invention in that the inside of the capillary part has been subjected to anti-reflection processing.

The object is also achieved in accordance with a development of the invention in that the chip holder is made of aluminum and the inside of the capillary part is subjected to black anodized aluminum processing.

In another embodiment of the invention, in the capillary there is a broadened part.

In still another configuration of the invention, $D_1 < D_2$ and $D_1/L_1 \leqq (D_2-D_1)/2L_2$ where $D_1$ is the maximum length which is perpendicular to the optical axis of the capillary part, $L_1$ is the length of the capillary part in the direction of the optical axis, $D_2$ is the maximum length which is perpendicular to the optical axis of the chamber for measuring absorbance, and $L_2$ is the distance between the end faces of the microchip which contain the chamber for measuring absorbance and which runs in the direction of the optical axis of the chamber for measuring absorbance.

In another configuration of the invention, the chip holder is formed of two components which mount the microchip, a groove being formed on the inside of at least one of the components and a capillary part being formed by joining the two components together.

Preferably, in the chip holder, after inserting the microchip into it, the optical axis of the capillary part of the chip holder is aligned with the optical axis of the chamber for measuring the absorbance of the microchip and the microchip is pressed by the elastic component against the chip holder and thus held.

Action of the Invention

By the invention described in the first aspect, the light which passes through the capillary part and which is incident in the chamber for measuring absorbance has a large proportion of parallel light. Therefore, the accuracy of measuring the absorbance can be increased compared to the case of not using a capillary part.

The proportion of parallel light can be increased, and thus, the accuracy for measurement of absorbance can be increased as compared to the case of not using a capillary by the anti-reflection and black anodized processing and by eliminating the light which is reflected within the capillary part.

By enlarging part of the capillary, the light which is reflected within the capillary part can be essentially completely eliminated.

Due to the described matching of the diameters and lengths, the light which has passed though the capillary on the front of the incidence opening of the chamber for measuring absorbance continues as desired and reaches the detector without colliding with the side of the chamber for measuring absorbance. Therefore, the absorbance can be measured with high accuracy, without error.

The capillary part can be easily formed in the chip holder by the chip holder being made from two halves.

By using an elastic component, when the microchip is inserted into the chip holder, the optical axis of the capillary part of the chip holder is brought into agreement with the optical axis of the chamber for measuring absorbance of the microchip. Furthermore, by means of the elastic component, the microchip is pressed onto the chip holder and held there. This prevents the microchip from falling out of the chip holder, and thus, a stable measurement of the absorbance can be taken.

The invention is further described below with reference to the accompanying drawings.

DETAILED DESCRIPTION OF THE INVENTION

Figure 4:
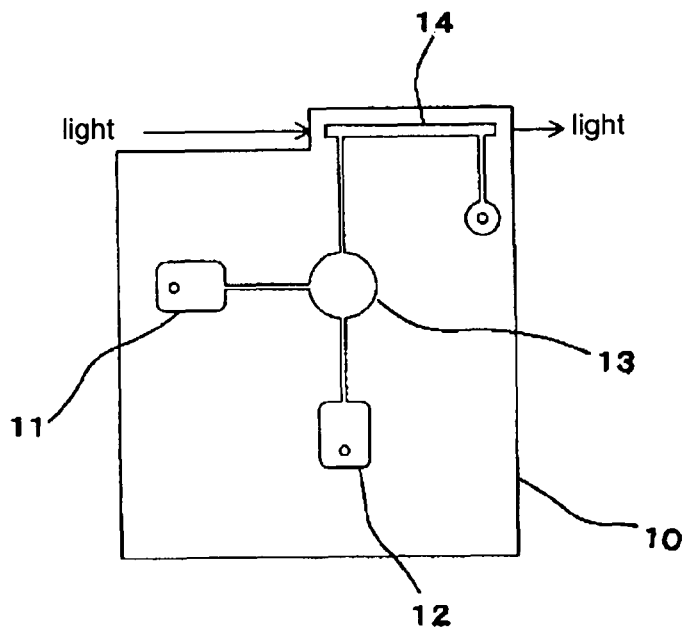
FIG. 4 shows a schematic of one example of the arrangement of a microchip for which the unit of the invention for measuring absorbance is used.

FIG. 4 schematically shows one example of the arrangement of a microchip 10 which can be used in a unit in accordance with the invention for measuring absorbance. The microchip 10 is made of a plastic material, for example, a thermoplastic resin, such as PMMA (polymethylmethacrylate), PET (polyethylene terephthalate), PC (polycarbonate) or the like, and a hot-setting adhesive, such as epoxy resin or the like. The microchip 10 is produced by cementing two plate components together. One of the adhesive surfaces is formed beforehand with a groove which defines a cavity when the plates are cemented together. Furthermore, there are a sample chamber 11 which is continuously connected to the area outside the chip and by which an analysis fluid can be delivered to the chip, a reagent chamber 12 which can be filled with a reagent for reaction with the analysis fluid, a reagent mixing chamber 13 for mixing the analysis fluid with the reagent, and a chamber for measuring absorbance 14 in which light from the outside is allowed to pass through the test fluid which was produced by mixing. The chamber for measuring absorbance 14 is located in a straight line along one end face of the plate components. In FIG. 4, the reagent chamber 12, the reagent mixing chamber 13, the chamber for measuring absorbance 14 and the like are located within the microchip 10, but they are shown using solid lines.

Figure 1:
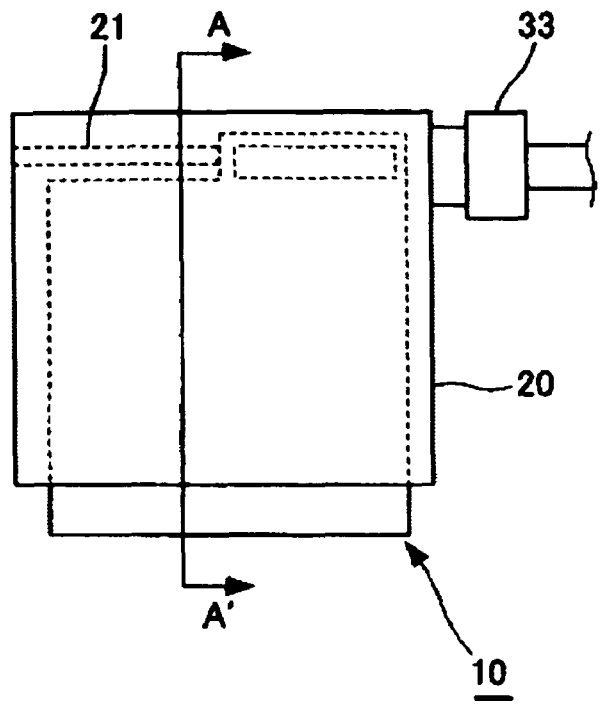
FIGS. 1(*a*) and 1(*b*) are, respectively, plan and cross-sectional schematic views of a unit in accordance with the invention for measuring absorbance for a microchip.
Figure 1:
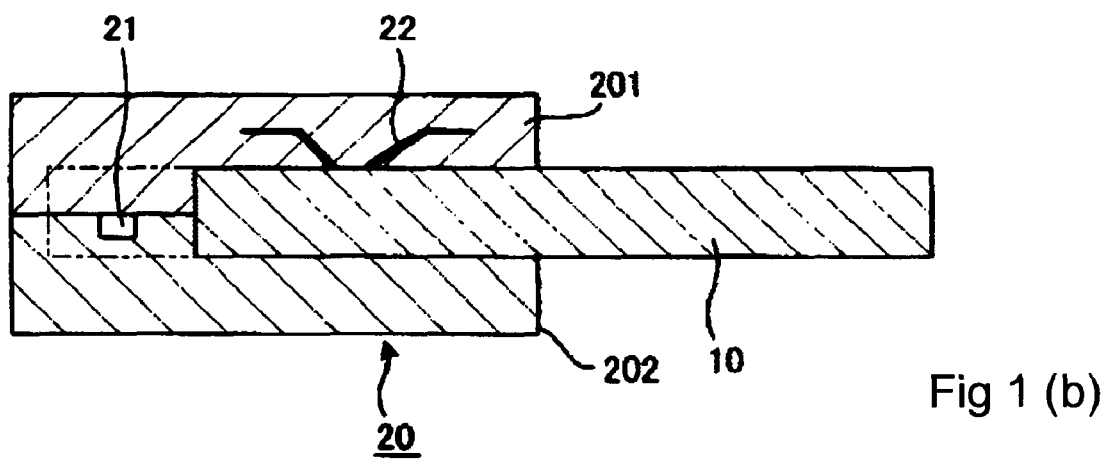

FIGS. 1(a) & 1(b) each show a unit in accordance with the invention for measuring the absorbance for a microchip. FIG. 1(a) shows the microchip 10 installed in the chip holder 20. The chip holder 20, as shown in FIG. 11(b), which is a cross section cut along the line A-A' in FIG. 1(a), comprises two components formed by division, the inside of one of the components being provided with a straight groove. By joining the two chip holder parts 201, 202, the capillary part 21 shown in FIG. 1(b) is formed. By joining of the two components, the capillary part 21 can be easily formed in the chip holder 20. Both components can also be provided with a groove.

Figure 9:
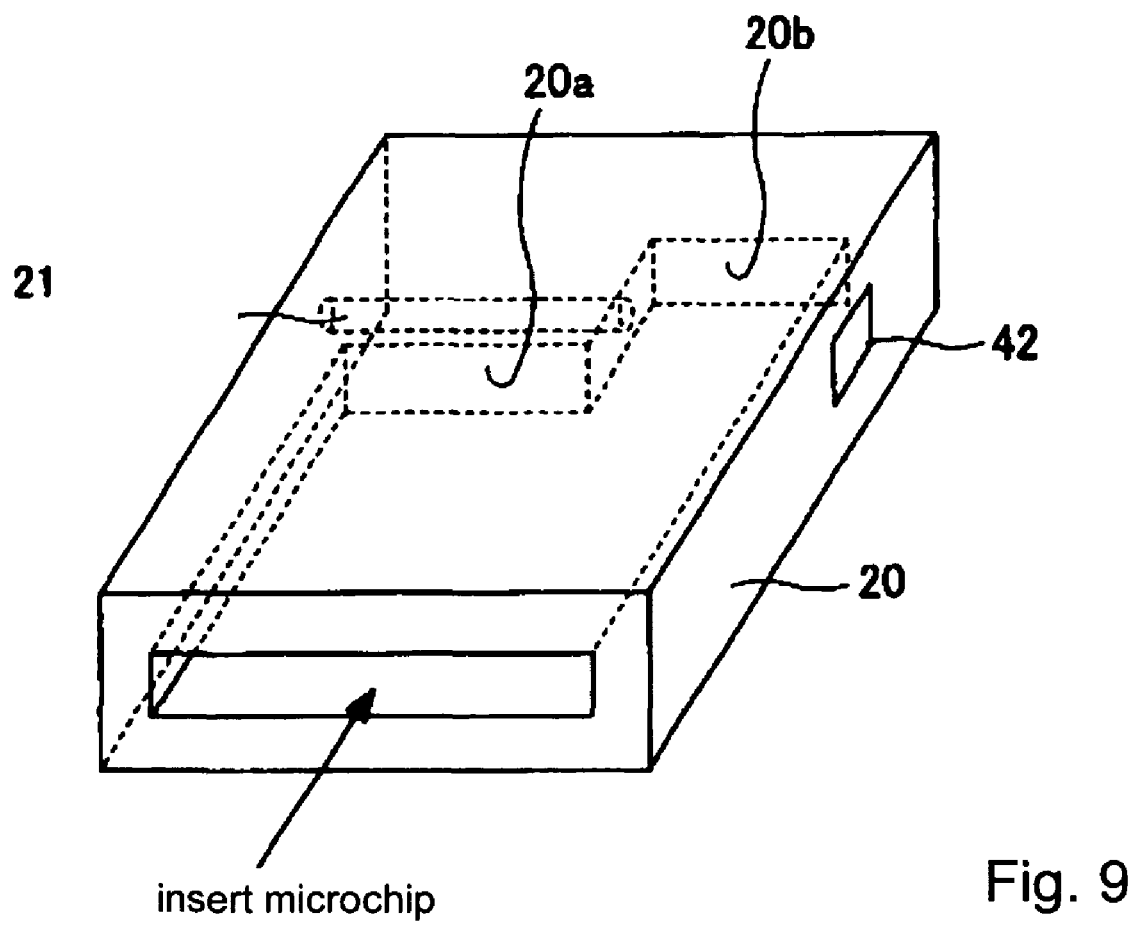
FIG. 9 shows a schematic perspective view of a chip holder for a unit in accordance with the invention for measuring absorbance.

FIG. 9 shows a schematic of the chip holder. A microchip (not shown in this figure) is inserted into the chip holder 20 in the direction of the arrow. The microchip abuts the inside walls 20a, 20b of the chip holder and is positioned in this way. In this way, the optical axis of the capillary part 21 of the chip holder 20 is aligned with the chamber 14 for measuring absorbance of the microchip. The microchip 10, as shown in FIG. 1(b), is pressed by means of an elastic component 22 against the chip holder 20 and is held there. The elastic component 22 is specifically a leaf spring. However, a rubber component or other elastic component can also be used for this purpose. In FIG. 9, 42 is the light exit part for the light receiving apparatus.

The diameter $D_1$ of the opening of the capillary part 21 is smaller than the diameter $D_2$ of the cross section of the chamber 14 for measuring absorbance which is perpendicular to the optical axis. For example, the diameter $D_1$ of the opening of the capillary part is 0.3 mm and the diameter $D_2$ of the cross section which is perpendicular to the optical axis of the chamber for measuring absorbance is 0.7 mm.

The optical axis of the capillary part is aligned with the optical axis of the chamber 14 for measuring absorbance. The light entering the capillary part 21 is light which was selected by a filter, as described below. This light passes through the capillary part 21, enters the absorbance measuring chamber 14, and is received by a light receiving component, such as a photodiode or the like. The light which passes through the capillary part and is incident in the chamber 14 for measuring absorbance has a large proportion of parallel light; this increases the accuracy of measuring the absorbance.

If the inside of the capillary part 21 is subjected to black anodization processing, when the inside of the capillary part is made, for example, of aluminum, the light reflected in the capillary part is reduced and light with higher parallelism can be delivered into the chamber for measuring absorbance.

Figure 7:
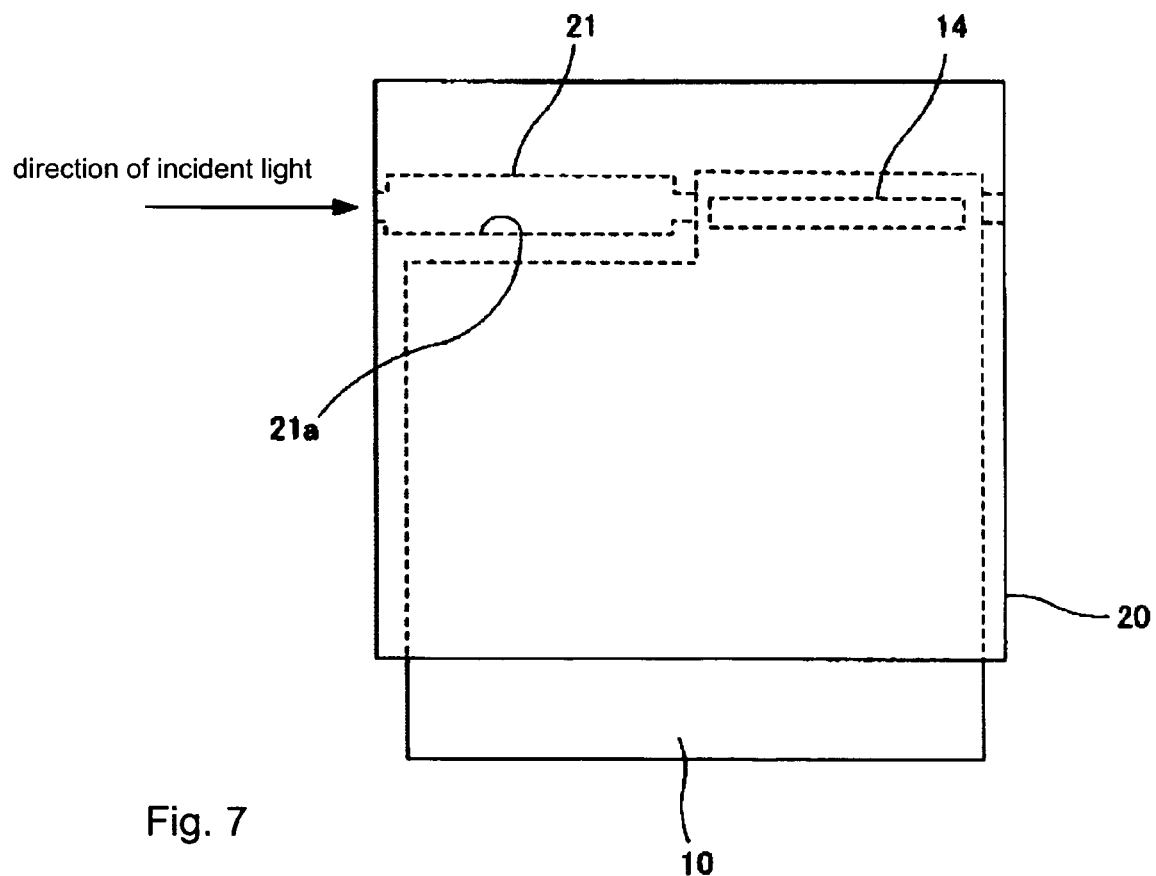
FIG. 7 shows a schematic of one example in which the diameter of the inside of the capillary part has been enlarged.

Furthermore, the middle area of the capillary can be enlarged by the arrangement of a part 21a of larger diameter within the capillary part 21, as is shown in FIG. 7, and the light reflected within the capillary part can be completely suppressed.

Figure 2:
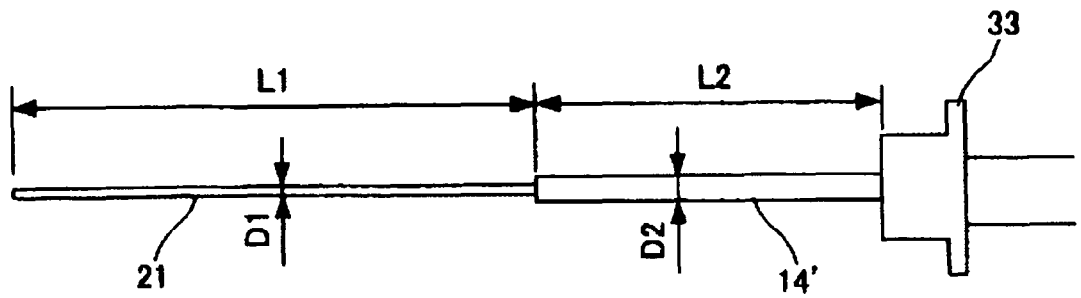
FIG. 2 is a schematic depiction of the relationship between the lengths and diameters of the chamber for measuring absorbance and the capillary part.

FIG. 2 shows the relation between the capillary part, the chamber for measuring absorbance and the light receiving apparatus. When comparison expressions $D_1 < D_2$ and $D_1/L_1 \leq (D_2 - D_1)/2L_2$ are satisfied, where $D_1$ is the maximum length which is perpendicular to the optical axis of the capillary part (diameter), $L_1$ is the length of the capillary part in the direction of the optical axis, $D_2$ is the maximum length which is perpendicular to the optical axis of the above described chamber for measuring absorbance (diameter), and $L_2$ is the distance between the end faces of the microchip which contain the chamber 14 for measuring absorbance and which runs in the direction of the optical axis of the chamber 14, the light which collides with the inside of the capillary part is eliminated and only the light which has passed through the capillary part is incident in the light receiving apparatus. Thus, the measurement accuracy is increased even more.

Figure 3:
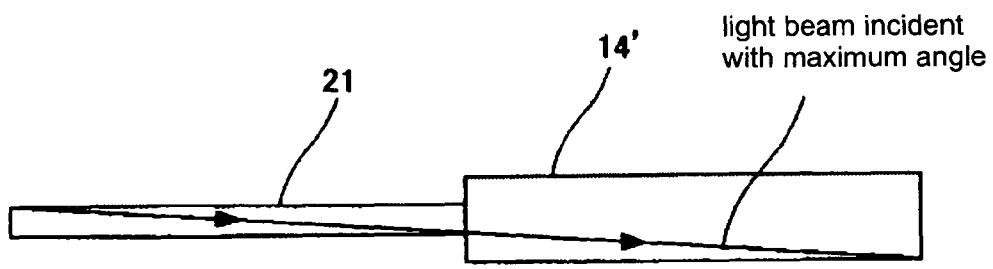
FIG. 3 represents the state in which the light incident from one end of the capillary part passes through the chamber for measuring absorbance.

FIG. 3 shows the state in which the light incident from the end of the capillary part passes through the chamber for measuring absorbance. In this state, as shown in FIG. 3, there is the relation $D_1/L_1 = (D_2 - D_1)/2L_2$. For the beam which was incident from the end of the capillary part in the capillary, the beam which was incident with the maximum angle travels to the end of the chamber for measuring absorbance without being reflected in the capillary part.

Figure 5:
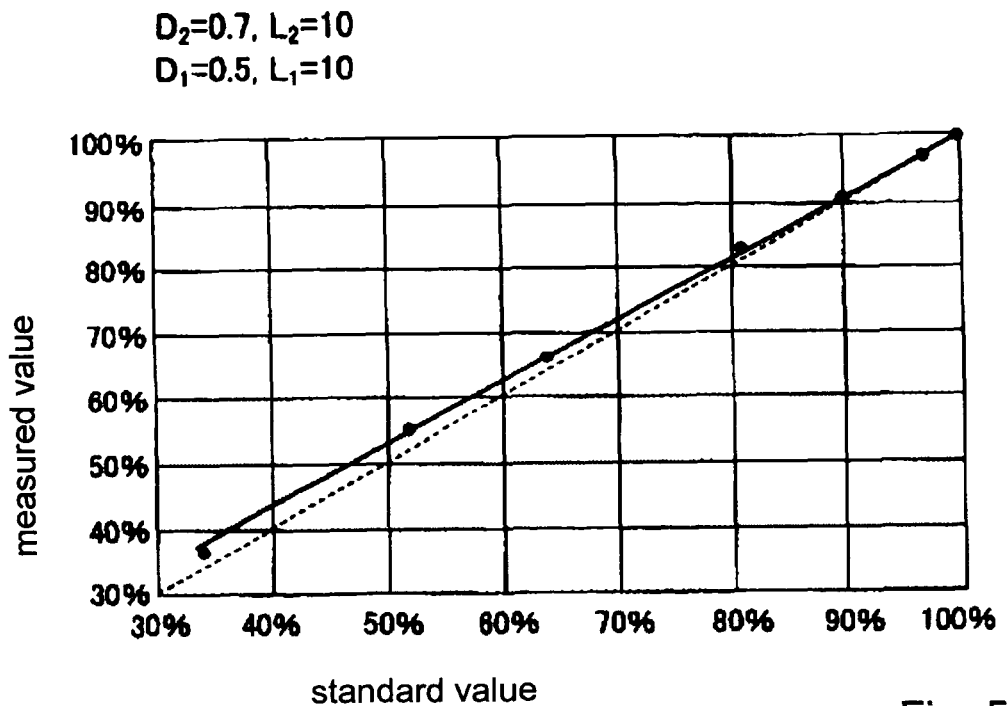
FIGS. 5(*a*) and 5(*b*) each are plots of the results of tests to confirm the effects of the invention.
Figure 5:
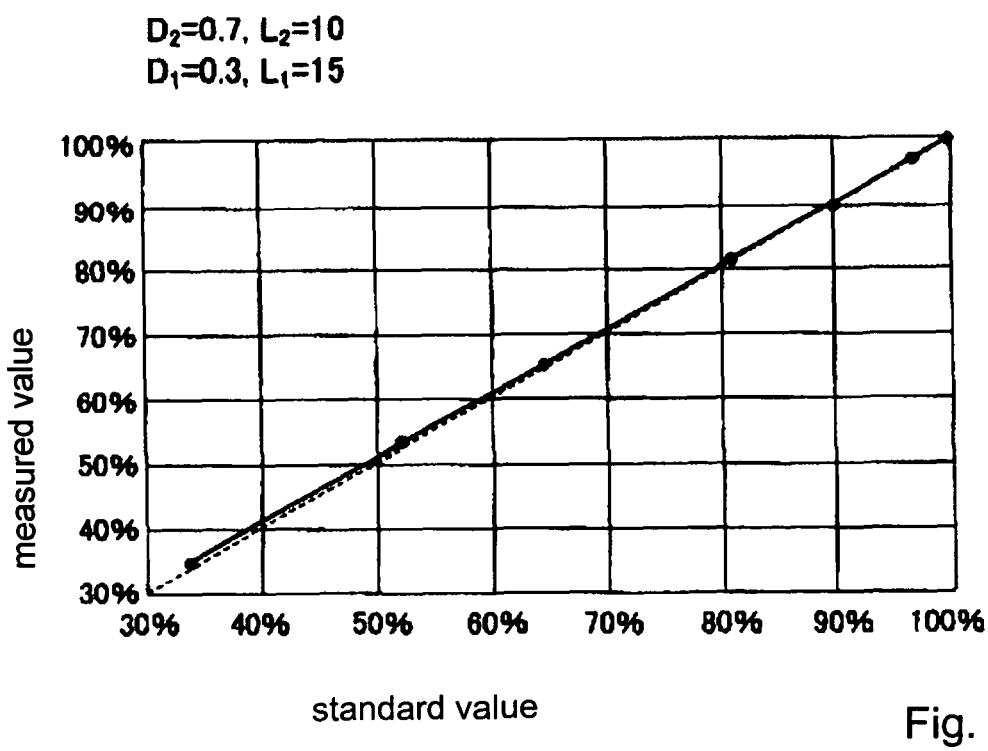
Figure 6:
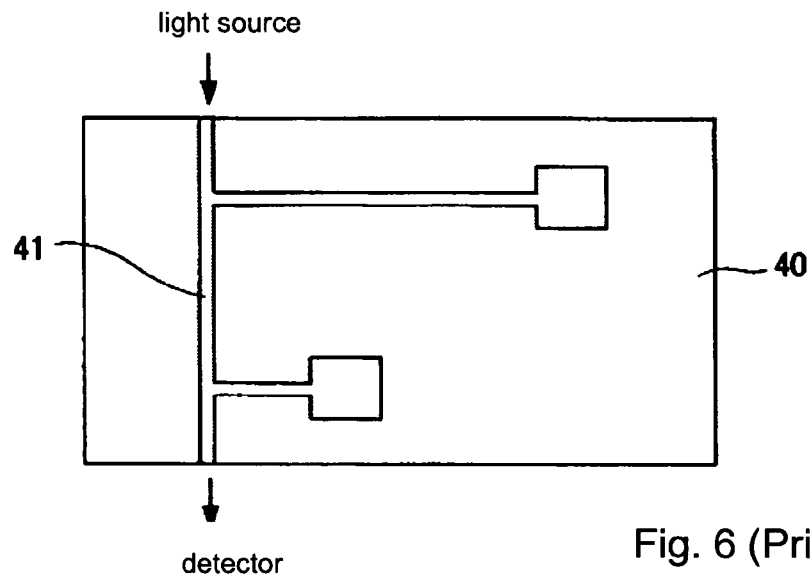
FIG. 6 is a schematic representation of light measurement with a conventional microchip.

FIGS. 5(a) and 5(b) each show the result of measurement tests which were carried out with respect to the above described formula to demonstrate the effect.

Figure 8:
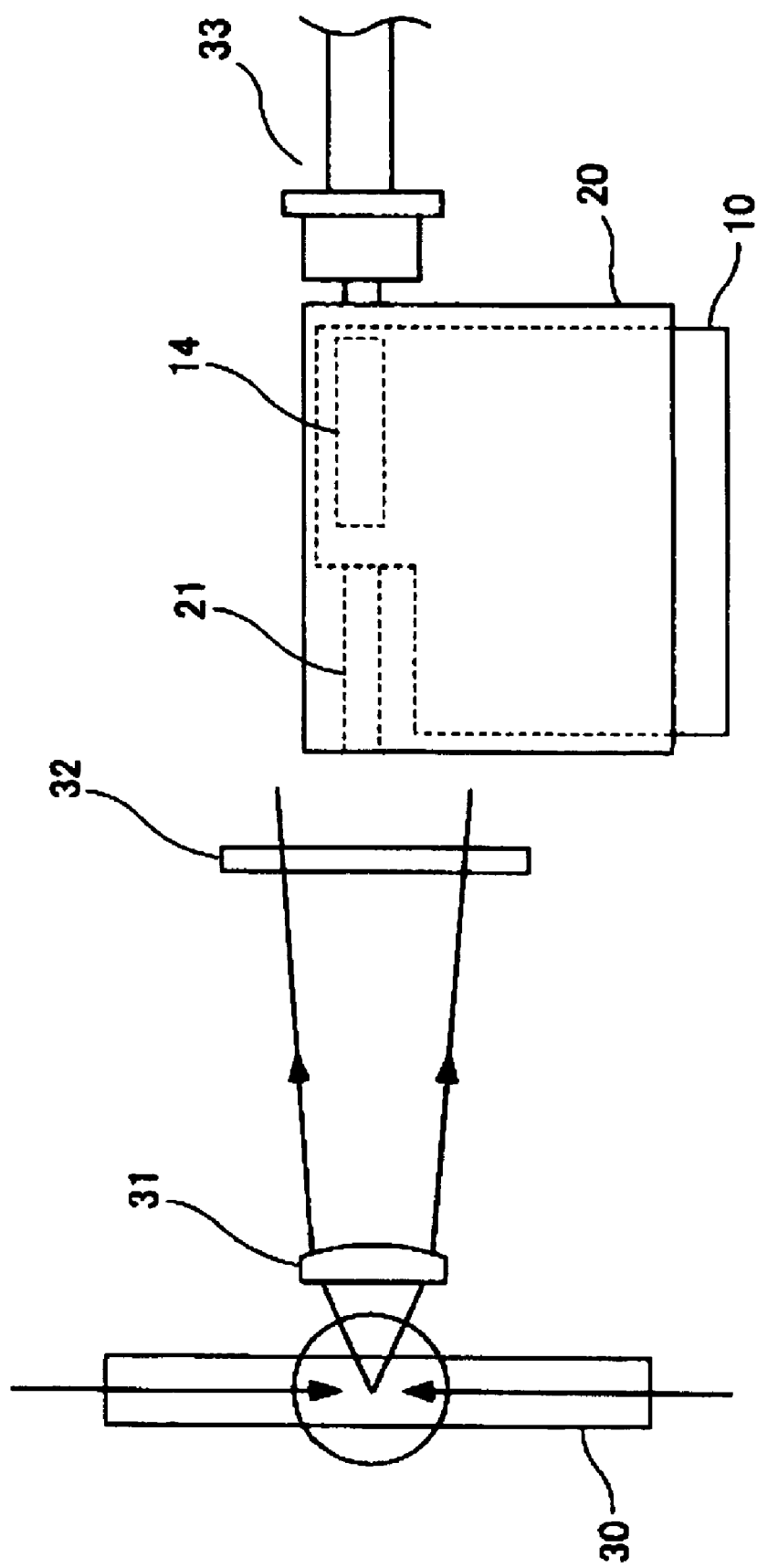
FIG. 8 is a schematic representation of an absorbance measurement system.

In the unit 10 for measuring the absorbance shown in FIG. 1(a) & 1(b), the chamber for measuring absorbance was filled with seven different solutions, specifically with pure water and with 5-amino-2-nitrobenzoic acid solutions (1 µmol/l, 5 µmol/l, 10 µmol/l, 20 µmol/l, 30 µmol/l, 50 µmol/l). The measurement system shown in FIG. 8 had a light source in which a xenon lamp 30, a lens 31 and a bandpass filter 32 were combined with one another, light with a primary wavelength of 405 nm (405±5 µm) was allowed to be incident from the capillary part 21, the light which passed through the chamber 14 for measuring absorbance was received by a light receiving apparatus 33 comprised of a silicon photodiode, and its attenuation factor was studied. This means that it was investigated how much of the light after attenuation reached the light receiving apparatus 33 where the amount of light measured when only pure water is placed in the chamber for measuring absorbance is considered 100%. The solution of 5-amino-2-nitrobenzoic acid exhibited absorption at a wavelength of roughly 405 nm. The amount of absorption changes depending on the concentration. The values in the figures show the value of the amount of light which has passed through the chamber 14 for measuring absorbance and was received by the light receiving apparatus 33 on a silicon photodiode. The line which has approached this value is the solid line in the figures. FIGS. 5(a) and 5(b) for the standard value show the respective values using a broken line in which the light with the primary wavelength of 405 nm (405±5 nm) was measured by means of a spectrophotometer after passage through the above described seven different solutions, specifically pure water and 5-amino-2-nitrobenzoic acid solutions (1 µmol/l, 5 µmol/l, 10 µmol/l, 20 µmol/l, 30 µmol/l, 50 µmol/l).

FIG. 5(a) shows a case of $D_1 < D_2$ and $D_1/L_1 < (D_2 - D_1)/2L_2$, where the maximum length $D_2$ which is perpendicular to the optical axis of the chamber for measuring absorbance is 0.7 mm, the distance $L_2$ between the end faces of the microchip which contain the above described chamber 14 for measuring absorbance and which runs in the direction of the optical axis of the chamber 14 for measuring absorbance is 10 mm, the maximum length $D_1$ which is perpendicular to the optical axis of the capillary part is 0.5 mm, and the length $L_1$ in the direction of the optical axis is 10 mm. The bilateral components comprising the microchip and clamping the chamber for measuring absorbance are each 1 mm.

FIG. 5(b) shows the invention. Here, for $D_1<D_2$ and $D_1/L_1>(D_2-D_1)/2L_2$, the maximum length $D_2$ which is perpendicular to the optical axis of the chamber for measuring absorbance is 0.7 mm, the distance $L_2$ between the end faces of the microchip which contain the above described chamber 14 for measuring absorbance and which runs in the direction of the optical axis of the chamber for measuring absorbance is 10 mm, the maximum length $D_1$ which is perpendicular to the optical axis of the capillary part is 0.3 mm, and the length $L_1$ in the direction of the optical axis is 10 mm. In FIG. 5(b), for each reagent, a light attenuation factor is shown which is essentially identical to the standard value (the value measured by the spectrophotometer). In FIG. 5(a), a result is obtained in which the light attenuation factor is higher than the standard value due to faulty light.

Furthermore, in the case of $D_1<D_2$ and $D_1/L_1=(D_2-D_1)/2L_2$, specifically in the case of the maximum length $D_2$ which is perpendicular to the optical axis of the chamber for measuring absorbance of 0.7 mm, of the distance $L_2$ between the end faces of the microchip which contain the chamber for measuring absorbance and which runs in the direction of the optical axis of the chamber 14 for measuring absorbance of 10 mm, of the maximum length $D_1$ which is perpendicular to the optical axis of the capillary part of 0.3 mm, and the length $L_1$ in the direction of the optical axis of 15 mm, it was confirmed by reagent with several different concentrations that, in any case, an attenuation factor was shown which is essentially identical to the standard value.

The above described circumstance confirms that by increasing the length and decreasing the diameter of the capillary chamber 21 in accordance with the relationships $D_1<D_2$ and $D_1/L_1 \leqq (D_2-D_1)/2L_2$, absorbance can be measured with high precision.

What is claimed is:

1. Unit for measurement of absorbance using a microchip, comprising:
    a microchip with a continuous cavity, a sample chamber, a reagent chamber, a reagent mixing chamber and an absorbance measuring chamber for measuring absorbance of light by a sample which is arranged in a straight line in an area of the continuous cavity; and
    a chip holder in which the microchip is located and which has a capillary part which is adapted and arranged for enabling light used for measuring absorbance to be delivered through the capillary part to the absorbance measuring chamber,
    wherein the capillary part has a smaller opening diameter than a diameter of a cross section of the absorbance measuring chamber which is perpendicular to an optical axis of the absorbance measuring chamber, and
    wherein an optical axis of the capillary part is aligned with the optical axis of the absorbance measuring chamber for measuring absorbance,
    wherein the maximum length which is perpendicular to the optical axis of the capillary part D1, the length of the capillary part in the direction of the optical axis L1, the maximum length which is perpendicular to the optical axis of the absorbance measuring chamber D2 and the distance between the end faces of the microchip which contain the absorbance measuring chamber and which runs in the direction of the optical axis of the absorbance measuring chamber L2 have values which fulfill both of the following relationships:

$D_1<D_2$ and $D_1/L_1<(D_2-D_1)/2L_2$ wherein the capillary part has a middle area of increased diameter relative to inlet and outlet end areas of the capillary part.

2. Unit for measuring the absorbance in accordance with claim 1, wherein the microchip comprises two plate components which are cemented together and between which a continuous cavity is located which runs along an end face of the plate components.

3. Unit for measuring the absorbance in accordance with claim 2, wherein the cavity is made in an area of an adhesive surface between the plate components.

4. Unit for measuring the absorbance in accordance with claim 1, wherein the inside of the capillary part has been subjected to antireflection processing.

5. Unit for measuring the absorbance in accordance with claim 1, wherein the chip holder is made of aluminum and the inside of the capillary part has been subjected to black anodization processing.

6. Unit for measuring the absorbance in accordance with claim 1, wherein the capillary part has a middle area of increased diameter relative to inlet and outlet end areas of the capillary part.

7. Unit for measuring the absorbance in accordance with claim 1 wherein the chip holder comprises two components which enclose the microchip, and wherein a groove is formed on the inside of at least one of the components which forms the capillary part.

8. Unit for measuring the absorbance in accordance with claim 1 wherein an elastic component is provided which presses the microchip against the chip holder.

9. Unit for measuring the absorbance in accordance with claim 1 wherein the inside of the capillary part has been subjected to antireflection processing.

10. Unit for measuring the absorbance in accordance with claim 1 wherein the chip holder is made of aluminum and the inside of the capillary part has been subjected to black anodization processing.

11. Unit for measuring the absorbance in accordance with claim 1, wherein the chip holder comprises two components which enclose the microchip, and wherein a groove is formed on the inside of at least one of the components which forms the capillary part.

12. Unit for measuring the absorbance in accordance with claim 1, wherein an elastic component is provided which presses the microchip against the chip holder.

* * * * *